(12) United States Patent
Rautiainen et al.

(10) Patent No.: US 11,697,789 B2
(45) Date of Patent: Jul. 11, 2023

(54) REACTOR FOR MANUFACTURING BIOGAS FROM ORGANIC RAW MATERIAL USING ANAEROBIC DIGESTION

(71) Applicant: Mika Rautiainen, 41310 Leppavesi (FI)

(72) Inventors: Mika Rautiainen, Leppavesi (FI); Annimari Lehtomaki, Petajavesi (FI)

(73) Assignee: Mika Rautiainen, Leppavesi (FI)

( * ) Notice: Subject to any disclaimer, the term of this patent is extended or adjusted under 35 U.S.C. 154(b) by 526 days.

(21) Appl. No.: 16/766,476

(22) PCT Filed: Nov. 23, 2018

(86) PCT No.: PCT/FI2018/050855
§ 371 (c)(1),
(2) Date: May 22, 2020

(87) PCT Pub. No.: WO2019/102074
PCT Pub. Date: May 31, 2019

(65) Prior Publication Data
US 2020/0377834 A1    Dec. 3, 2020

(30) Foreign Application Priority Data
Nov. 23, 2017   (FI) ..................................... 20176050

(51) Int. Cl.
| | |
|---|---|
| *C12M 1/107* | (2006.01) |
| *C12M 1/12* | (2006.01) |
| *C12M 3/00* | (2006.01) |
| *C05F 17/936* | (2020.01) |

(52) U.S. Cl.
CPC ............ *C12M 21/04* (2013.01); *C12M 23/06* (2013.01); *C12M 23/48* (2013.01); *C05F 17/936* (2020.01)

(58) Field of Classification Search
CPC .............................. C12M 21/04; C05F 17/936
See application file for complete search history.

(56) References Cited

U.S. PATENT DOCUMENTS

| | | | |
|---|---|---|---|
| 2015/0093811 A1* | 4/2015 | Peters | ................... C12M 27/06 435/283.1 |
| 2016/0130544 A1 | 5/2016 | Kientz | |
| 2016/0298067 A1* | 10/2016 | Rautiainen | .............. C12P 5/023 |

FOREIGN PATENT DOCUMENTS

| | | |
|---|---|---|
| CN | 202337784 | 7/2012 |
| CN | 106609240 | 3/2017 |
| CN | 106609238 | 5/2017 |
| DE | 20318783 | 4/2005 |
| DE | 202006014149 | 1/2007 |
| EP | 023176 | 1/1981 |

(Continued)

*Primary Examiner* — Jonathan M Hurst
(74) *Attorney, Agent, or Firm* — Fasth Law Offices; Rolf Fasth

(57) ABSTRACT

The reactor is for manufacturing biogas from organic raw material using anaerobic digestion. The reactor includes a tubular reaction chamber with a substantially rectangular cross-section composed of a bottom, walls and a ceiling for processing raw material into end products. Agitation and transfer equipment are arranged in the reaction chamber and an external support frame structure is arranged on the outer surface included in the reaction chamber for stiffening and supporting the reaction chamber externally against forces generated by the raw material.

16 Claims, 14 Drawing Sheets

(56) References Cited

FOREIGN PATENT DOCUMENTS

| | | | | |
|---|---|---|---|---|
| EP | 3638767 B1 * | 3/2021 | .............. | C02F 11/04 |
| WO | 2012067547 | 5/2012 | | |
| WO | 2015075298 | 5/2015 | | |

* cited by examiner

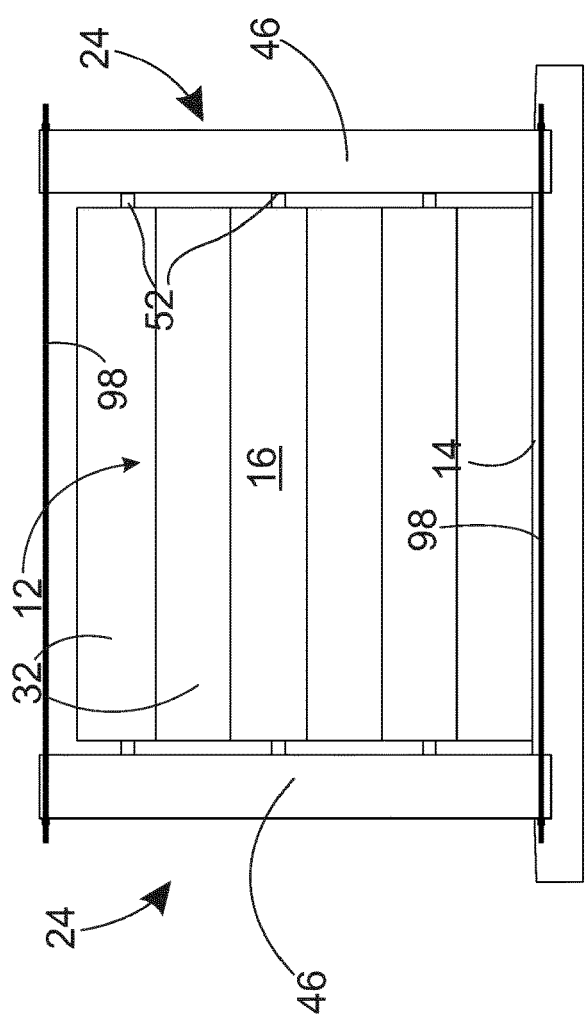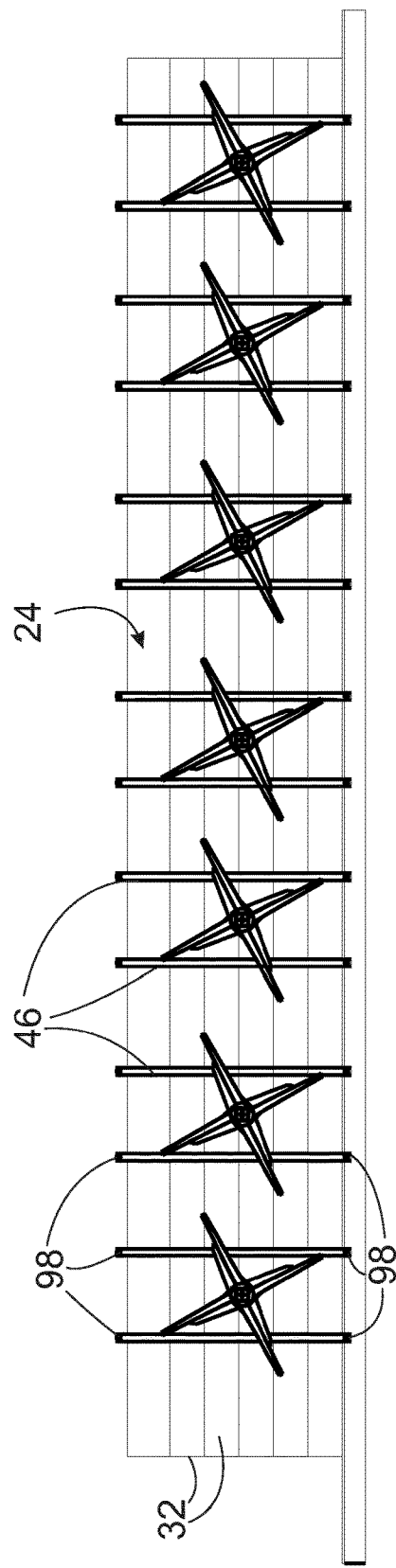

REACTOR FOR MANUFACTURING BIOGAS FROM ORGANIC RAW MATERIAL USING ANAEROBIC DIGESTION

PRIOR APPLICATIONS

This is a US national phase patent application that claims priority from PCT/FI2018/050855 filed 23 Nov. 2018, that claims priority from Finnish Patent Application No. 20176050, filed 23 Nov. 2017.

The invention is related to a reactor for manufacturing biogas from organic raw material using anaerobic digestion, the reactor including a tubular reaction chamber having a substantially rectangular cross-section composed of a bottom, walls and a ceiling for processing raw material into end products, and agitation and transfer equipment arranged in the reaction chamber.

Publication WO 2015/075298 A1 represents prior art proposing a reactor for producing biogas from biowaste. The reaction chamber is a tubular structure composed of walls, a floor and a ceiling. The reaction chamber is assembled be welding together steel components so that the reaction chamber resists the internal hydrostatic pressure exerted on it, generated by biowaste with a high water content during the slow anaerobic digestion reaction. In relatively small reactors with a maximum height of 2 m, hydrostatic pressure remains fairly low and the reaction chamber can be manufactured as a fairly thin construction with the wall thickness ranging between 100 mm and 150 mm.

However, a problem in a construction according to the aforementioned publication is that as the reactor size increases, the height of the raw material mattress in the reaction chamber also increases and thereby, the hydrostatic pressure exerted on the walls of the reaction chamber increases. To be able to make the reaction chamber sufficiently strong to resist stresses acting on it, the thickness of the walls of the reaction chamber must be increased proportionally to the increase of the reactor height. It is not reasonable to increase the width of reactors, since then the floor area they require at production plants would increase raising the need of covered space in the production plant and thereby investment costs. In turn, increasing the thickness of reaction chamber walls raises raw material costs, complicates the handling of the reaction chamber and causes high costs when the reaction chamber is transported as a whole from the place of manufacture to the application site.

Publication US 2016/0130544 A1 also represents prior art proposing a reaction chamber with a circular cross-section. A circular reaction chamber is, however, notably better in strength than a reaction chamber with a substantially rectangular cross-section, wherein great stresses are exerted particularly on the angles of the reaction chamber. In addition, a circular shape enables elastic flexibility of the reaction chamber.

Publication WO 2012067547 A1 also represents prior art proposing a reaction chamber surrounded by a support frame. However, such a construction is difficult to scale to larger size classes and scaling is performed by duplicating reactors.

The object of the invention is to provide a reactor for manufacturing biogas from organic raw material using anaerobic digestion that is more advantageous for its manufacturing and transport costs than prior art reactors. The characteristic features of this invention are set forth in the appended claim 1.

This object can be achieved with a reactor for manufacturing biogas from organic raw material using anaerobic digestion, the reactor including a tubular reaction chamber with a substantially rectangular cross-section composed of a bottom, walls and a ceiling for processing raw material into end products, and an external support frame structure arranged on the outer surface included in the reaction chamber for stiffening and supporting the reaction chamber externally against the forces generated by raw material.

In the reactor according to the invention, the reaction chamber with a substantially rectangular cross-section supported with an external support frame structure can be manufactured quite lightweight and with a thickness of even below 200 mm. This reduces the material costs and transfer costs of the reactor's reaction chamber compared to thicker reaction chambers with substantially rectangular cross-sections. On the other hand, the construction of the reaction chamber is also more affordable to implement than prior art reaction chambers with circular cross-sections. The external support frame structure can be made, for example, of tubular beams by assembling to an extremely rigid, yet fairly light structure, which supports the reaction chamber from outside. Thus, with the external frame structure, a counterforce is created for the force generated by the hydrostatic pressure inside the reaction chamber. The use of an external support frame structure enables upscaling of the reaction chamber to an extremely large size class while using a single reaction chamber, however, without increasing the wall thickness of the reaction chamber. The external support frame structure can also be a support structure integrated into the outer surface of the reaction chamber walls.

The reactor is advantageously a plug-flow reactor. In this case, the process can be continuously operating.

Advantageously, at least the walls and the ceiling of the reaction chamber are composed of modularly dimensioned elements. In this case, a large-size reaction chamber is easy to transport from the place of manufacture to the application site as notably smaller elements. The use of elements is particularly advantageous with an external support frame structure, since the connections between the elements do not then need to receive transverse forces as is the case in prior art reactors implemented without an external frame structure. On the other hand, a reaction chamber made of elements is easily scalable to a preferred size class.

The height of the reactor may be in the range of 3 m-15 m, preferably 5 m-10 m. Hydrostatic pressure generated by liquid material in the reaction chamber produces extremely high forces as the reactor height increases when aiming for a higher capacity. Great hydrostatic forces are exerted particularly on the connections between the bottom and the walls of a reaction chamber with a substantially rectangular cross-section; these connections can be supported, according to the invention, with an external frame structure.

Advantageously, the reaction chamber has a rectangular cross-section. Thus, the elements forming the reaction chamber can be rectangular.

Modularly dimensioned elements on the reaction chamber walls can have a height ranging between 1.0 m-3.6 m, preferably 1.2 m-2.4 m. In this way, the elements are easier to handle than large elements and they can be tightly packed in conventional marine containers minimising the empty space that remains in the marine container.

Modularly dimensioned elements on the walls of the reaction chamber can have a length of 6 m-13 m, preferably 10 m-12 m. In this way, the elements are easier to handle than large elements and they can be tightly packed in conventional marine containers minimising the empty space that remains in the marine container.

Advantageously, agitation and transfer equipment is supported to the elements. With agitation and transfer equipment, raw material can be mixed for optimising biological action, as well as moved ahead in the reaction chamber for promoting anaerobic digestion.

Advantageously, agitation and transfer equipment is supported to the elements in the transverse direction relative to the reaction chamber. In this case, the reactor may include separate agitation zones, which can enhance the efficiency of biogas production.

Advantageously, agitation and transfer equipment comprise multiple blade agitators. Multiple blade agitators can be controlled each one independently by forming independent agitation blocks, where agitation can be optimised in each one according to the needs of the agitation block concerned.

According to an embodiment, the external support frame structure comprises vertical columns arranged at a distance from each other in the lengthwise direction relative to the reactor on both sides of the reactor, transverse support structures for connecting the vertical columns on each side of the reaction chamber in the transverse direction relative to the reactor, and longitudinal support structures for connecting the vertical columns to each other in the lengthwise direction relative the reactor on each side of the reactor. Each vertical column includes two vertical supports set at a distance from each other in the transverse direction relative to the reaction chamber and transverse supports arranged between the vertical supports. With such a construction, the support frame structure can be made very rigid, although the materials used for the support frame structure can be relatively light in weight. On the other hand, vertical columns composed of vertical supports and transverse supports are independently rigid constructions and therefore do not need separate transverse supports for receiving forces acting in the transverse direction relative to the reaction chamber. Such a construction enables scaling of the reaction chamber to quite large dimensions.

According to an embodiment, the bottom of the reaction chamber includes footings for the vertical columns of the support frame structure. In this way, the vertical columns can be securely supported at their bottom ends, while the top ends are advantageously supported over the reaction chamber with transverse support structures.

The bottom of the reaction chamber is advantageously concrete and the walls and the ceiling are steel constructions. A bottom cast of concrete can be used to fasten the parts of the support frame structure fixedly to the ground, whereas the manufacture of the walls and ceiling of the reaction chamber as steel constructions enables easy scalability.

According to another embodiment, the elements are made of concrete by casting and comprise an external support frame structure integrated into the outer edge.

The support frame structure is advantageously arranged to form the only horizontal support for the reaction chamber walls. In other words, the support frame structure is not below the reaction chamber. Thus, the bottom of the reaction chamber can be supported directly to the ground or the room floor, in which case it does not need to have a corresponding strength as would be required for a bottom resting partly on the support frame structure.

The reactor advantageously also includes heating, reject recirculation, automation and gas recovery equipment similar to that of prior art. With the heating equipment, the reaction chamber temperature is kept sufficiently high for anaerobic digestion. In turn, digestate is advantageously recirculated always to the previous agitation zone for transferring a microbial strain. An automation system is used to control the agitation and transfer equipment, heating equipment and reject recirculation equipment for maintaining anaerobic digestion in a preferably continuous process. The aforementioned components can be similar to those proposed in the prior art publication WO 2015/075298 A1.

The reaction chamber advantageously includes sealed leadthroughs for agitation and transfer equipment for keeping liquid raw material or end products in the reaction volume. This enables a sufficiently high filling rate for the reaction chamber in order to achieve good efficiency.

Advantageously, each element includes seals for sealing the seams between the elements. In this way, the elements can be made tight avoiding discharge of hydrostatic pressure in the reaction chamber between the elements.

The thickness of the walls (shell) of the reaction chamber can be in the range of 100 mm-300 mm, preferably 110 mm-160 mm. Thus, the weight of the reaction chamber remains moderate reducing transport costs and lowering material costs during the reactor manufacture.

Advantageously, the external support frame structure is composed of angle irons or tubular beams that are welded together. Angle irons and tubular beams are sufficiently rigid components to offer adequate stiffness, yet notably light to save weight and material. Instead of steel, the external support frame structure can be made, for example, of composite or other similar material with sufficient rigidity.

Advantageously, each element includes an edged reinforcement arranged to circulate the element for reinforcing it. With reinforcements, it is possible to increase the stiffness and load bearing capacity of the elements.

Advantageously, the external support frame structure includes plate stiffeners fastened against the outer surface of the reaction chamber. Due to the plate stiffeners, the external support frame structure stiffens the reaction chamber in such a way that it can be supported at selected points only and the external support frame structure can be quite sparse as to its vertical columns.

Plate stiffeners are advantageously fastened between edged reinforcements in each element. Thus, each element is sufficiently stiff to receive forces acting on it.

The external support frame structure is advantageously composed of hollow tubes fastened together. In this way, the weight of the external support frame structure remains moderate compared to a structure manufactured from solid iron, while, on the other hand, tubes provide sufficient structural rigidity to support the reaction chamber. Correspondingly, the external support frame structure can also be manufactured, for example, from composite or similar material.

Advantageously, the elements forming the reaction chamber are sandwich elements provided with a stiffening casing and insulation. These are extremely lightweight structures.

The thicknesses of the steel casings of the lower-most elements of the reaction chamber may be in the range of 6 mm-10 mm, when the reactor height is 5 m-12 m.

According to an embodiment, each element includes bolt holes formed in the casing for fastening the elements to each other with bolts, a first reinforcement plate provided with an opening for the bolt corresponding to the bolt hole, welded at each bolt hole, and a second reinforcement plate welded to the second element, to the side of the first reinforcement plate relative to the first reinforcement plate, for receiving lateral forces exerted on the bolt hole. The first reinforcement plate and the second reinforcement plate receive the horizontal loads applied to the bolt hole in the casing. Thus, it is not necessary to increase the thickness of the casing to achieve sufficient strength.

Advantageously, the elements are locked together on top of each other with the bolts of the bolted jointed. The use of bolts reduces the need of welding and facilitates the installation of the reactor.

Advantageously, the external support frame structure is arranged to extend in the vertical direction lower than the bottom of the reaction chamber, and the reactor includes a cable arranged through the bottom in the horizontal direction, fastened to the support frame structure on both sides of the reaction chamber for receiving horizontal forces with the external support frame structure. With the cable, it can be ensured that forces exerted on the bottom end of the external support structure can be efficiently received.

Implementation of a reaction chamber of a reactor according to the invention advantageously with elements enables transportation of the reactor in marine containers and delivery of reactors larger than before to customers located in poorly accessible regions. In turn, an external support frame structure provides the benefit that it is not necessary to increase thickness of wall of the reaction chamber even though the size of the reactor is increased.

The invention is described below in detail by making reference to the appended drawings that illustrate some of the embodiments of the invention, in which.

Figure 1:
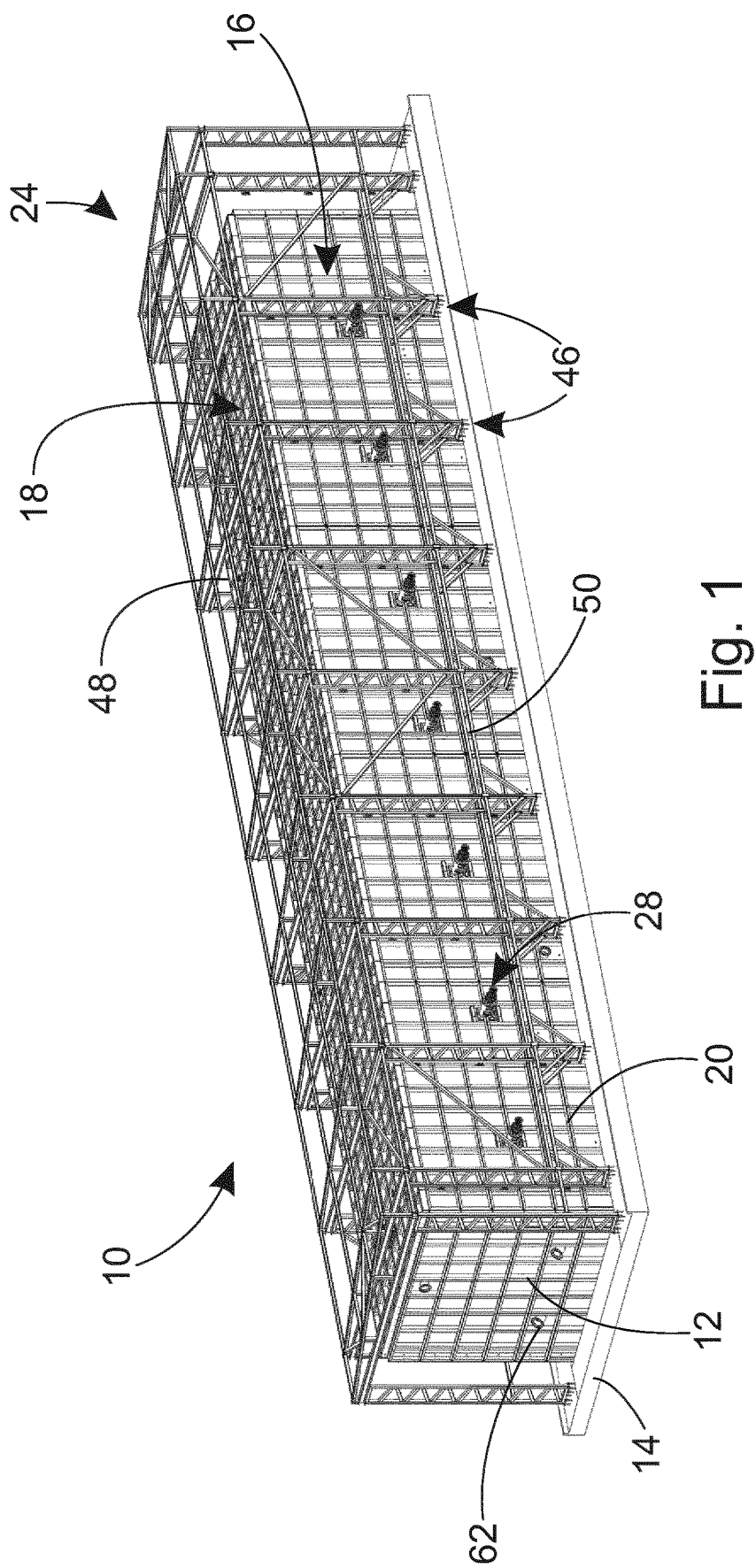
FIG. 1 is an axonometric view of a reactor according to the invention.
Figure 3A:
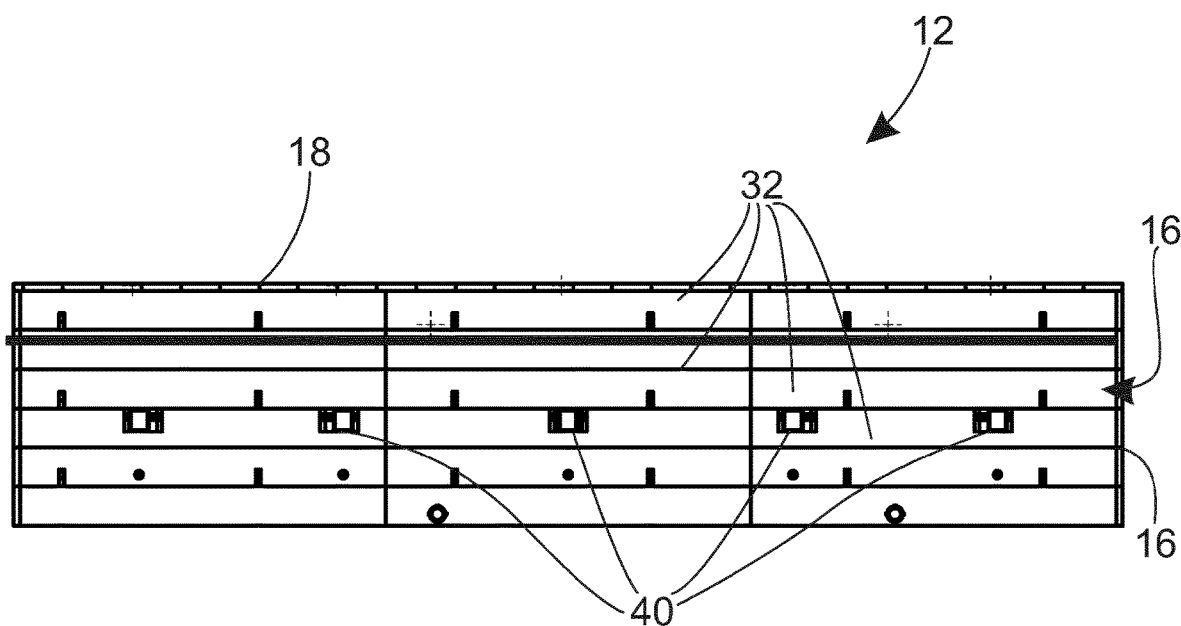
Figure 3B:
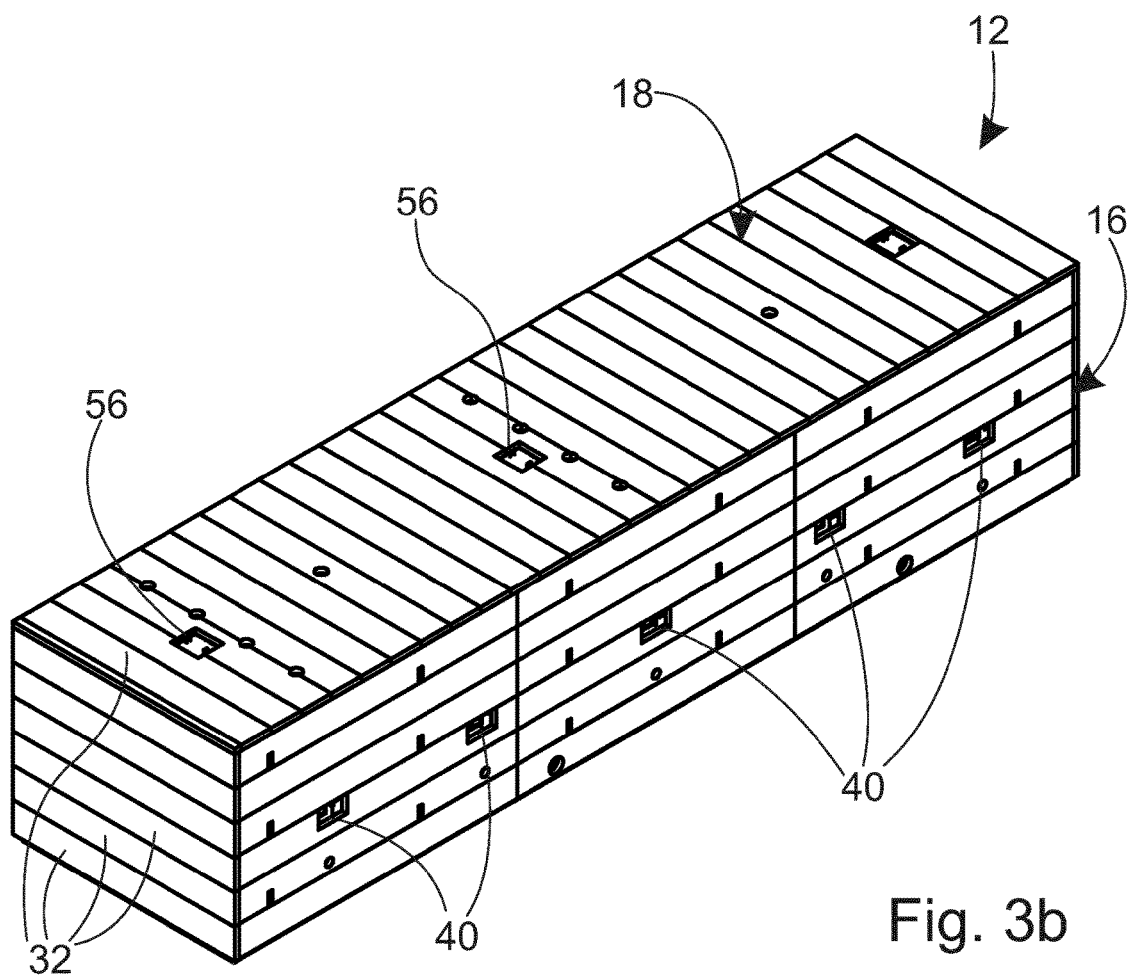
Figure 4A:
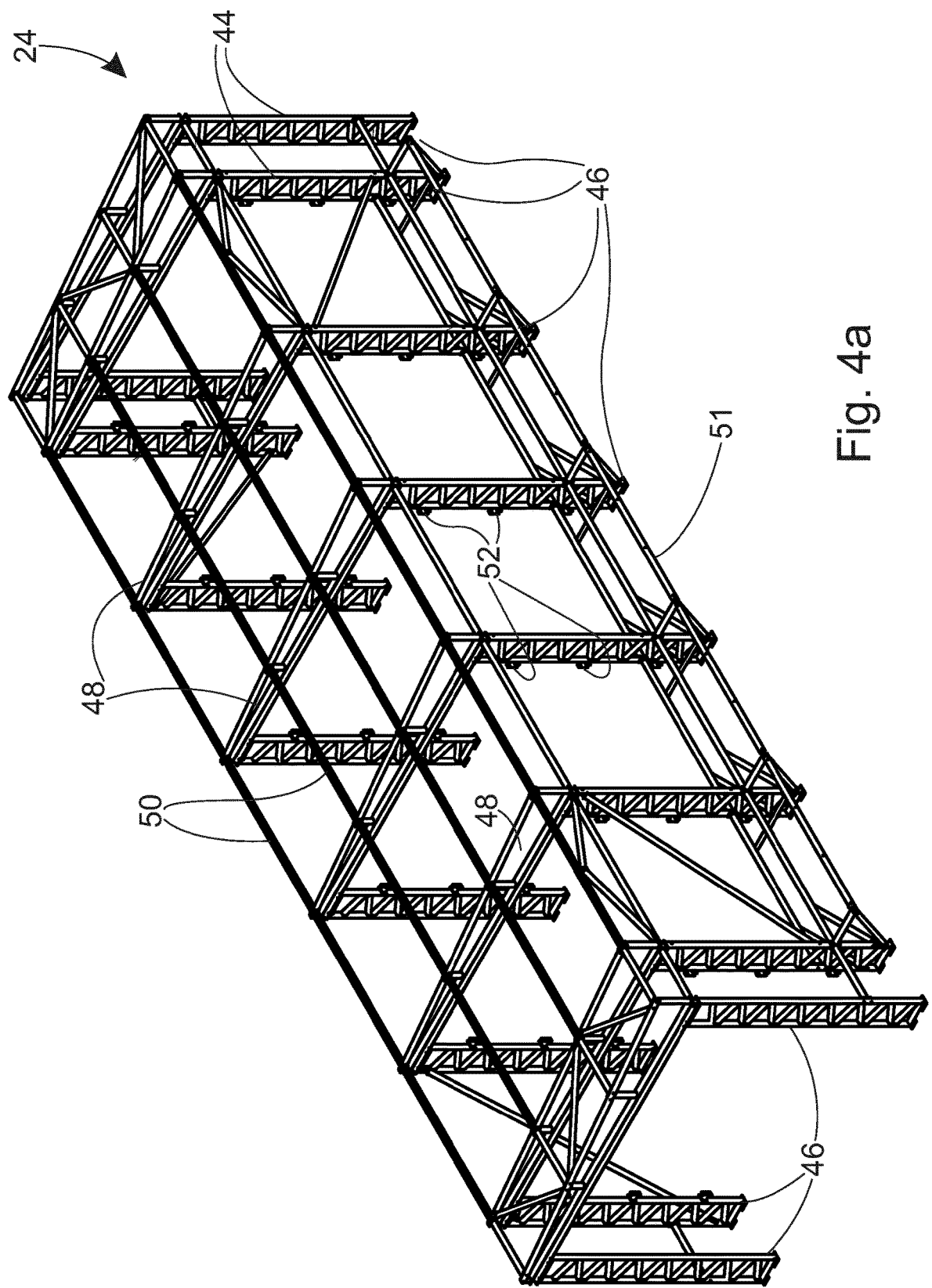
Figure 4B:
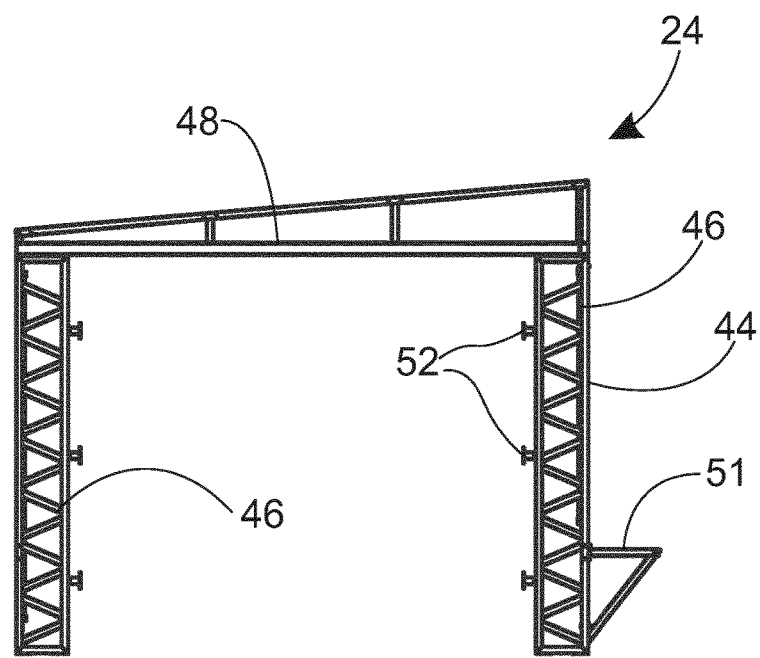
Figure 4C:
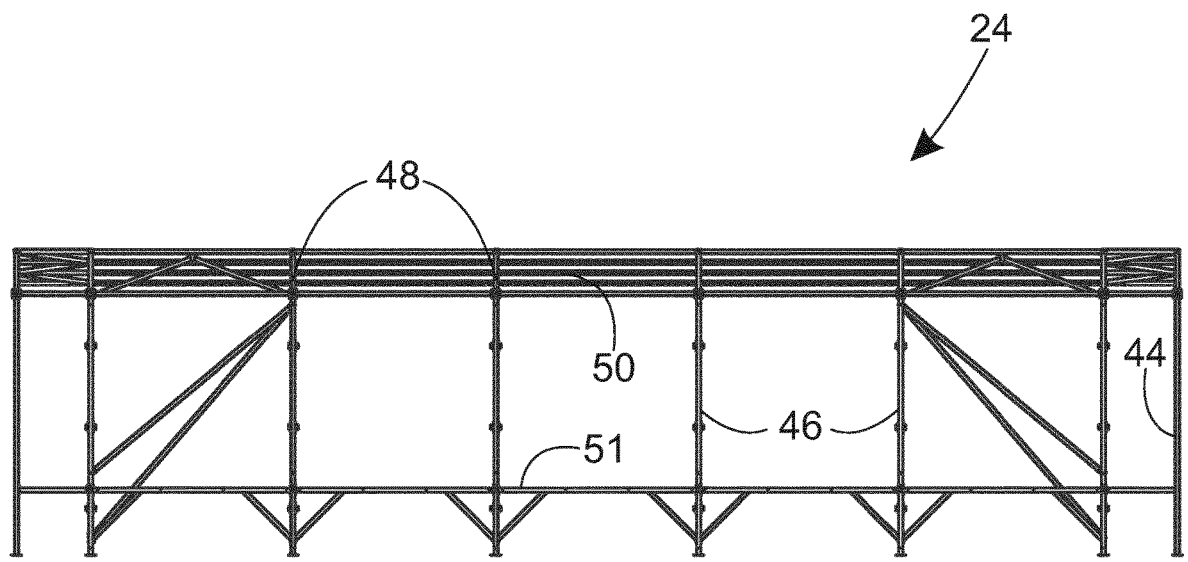
Figure 5:
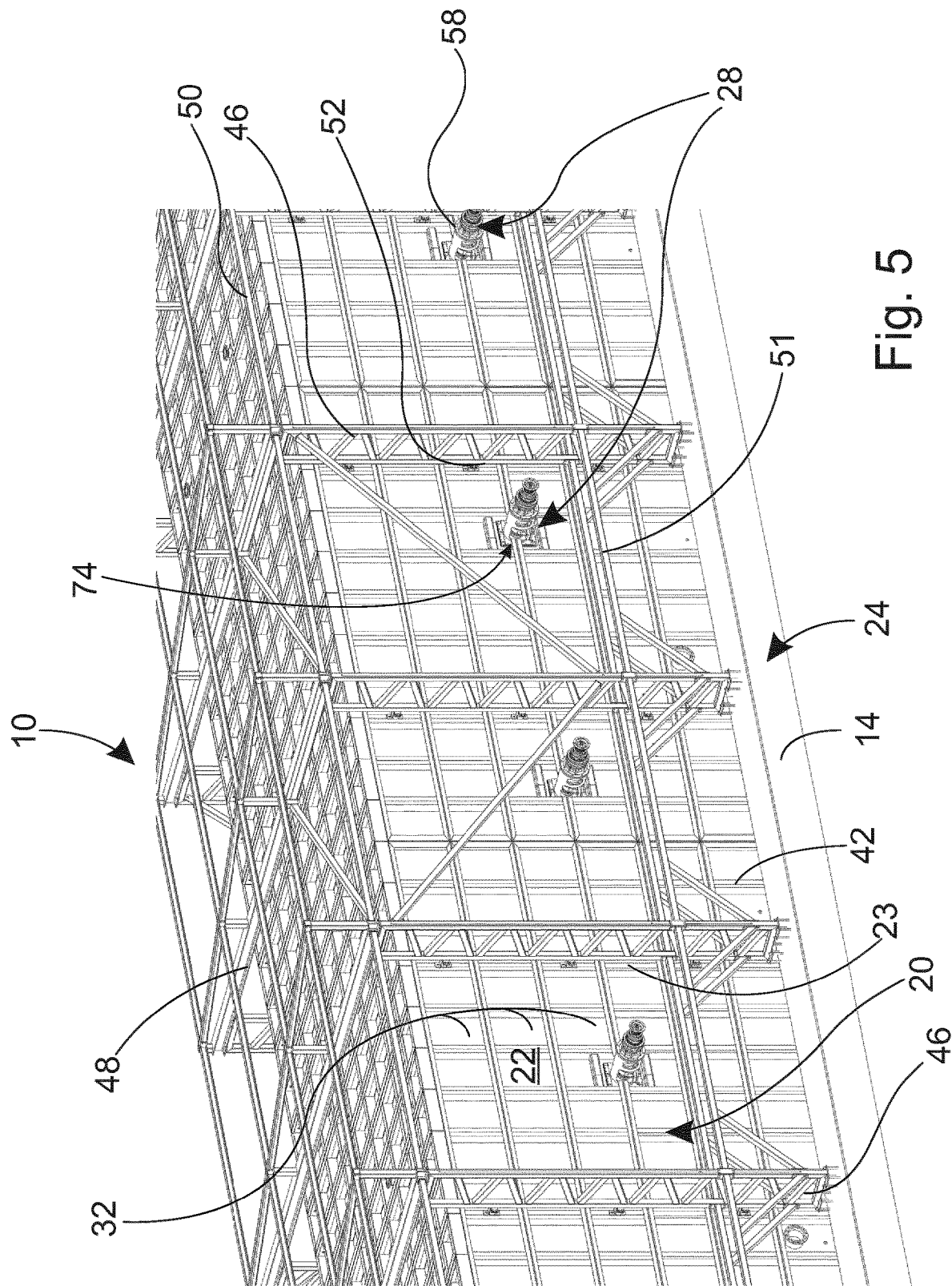
Figure 6:
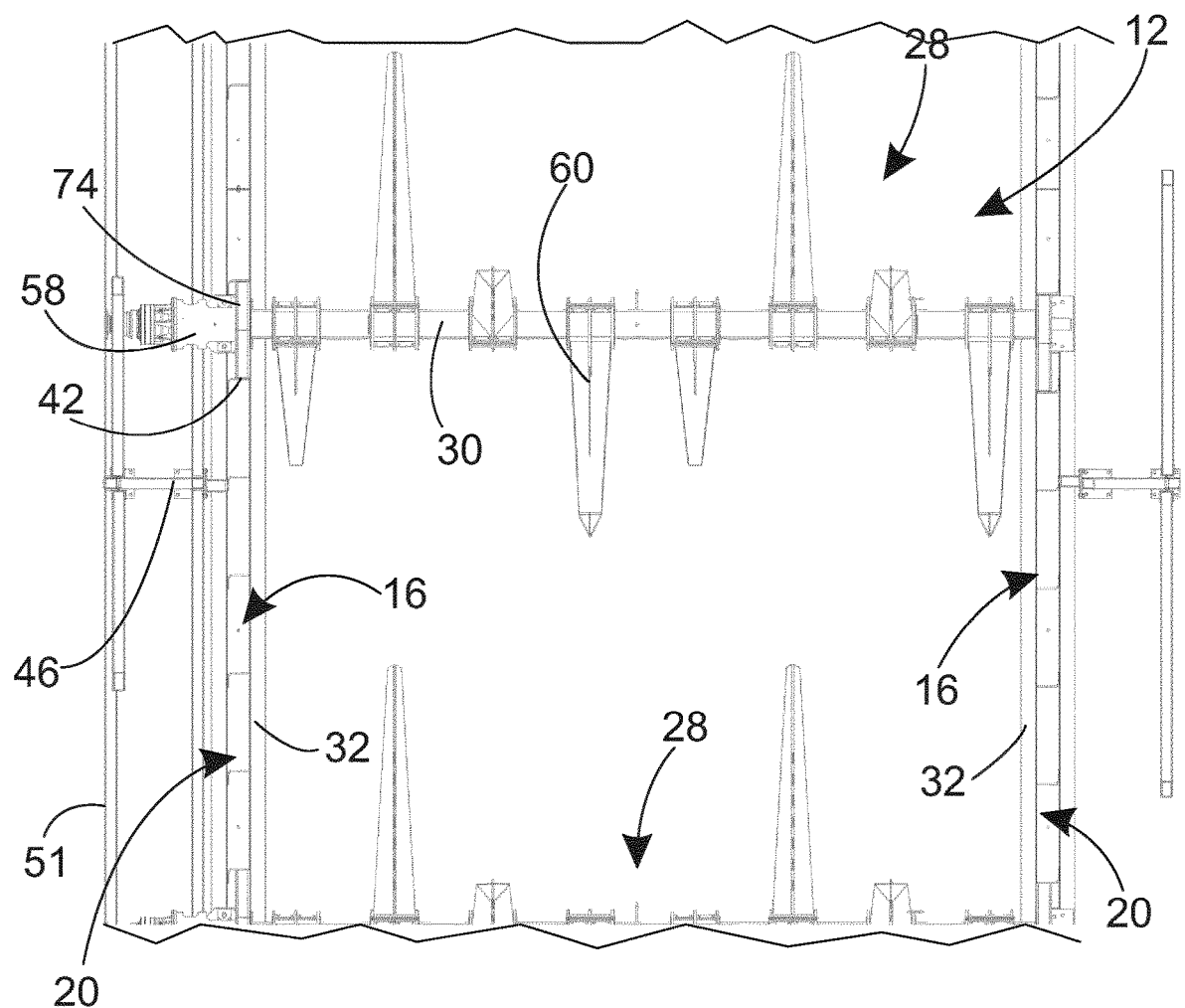
Figure 7:
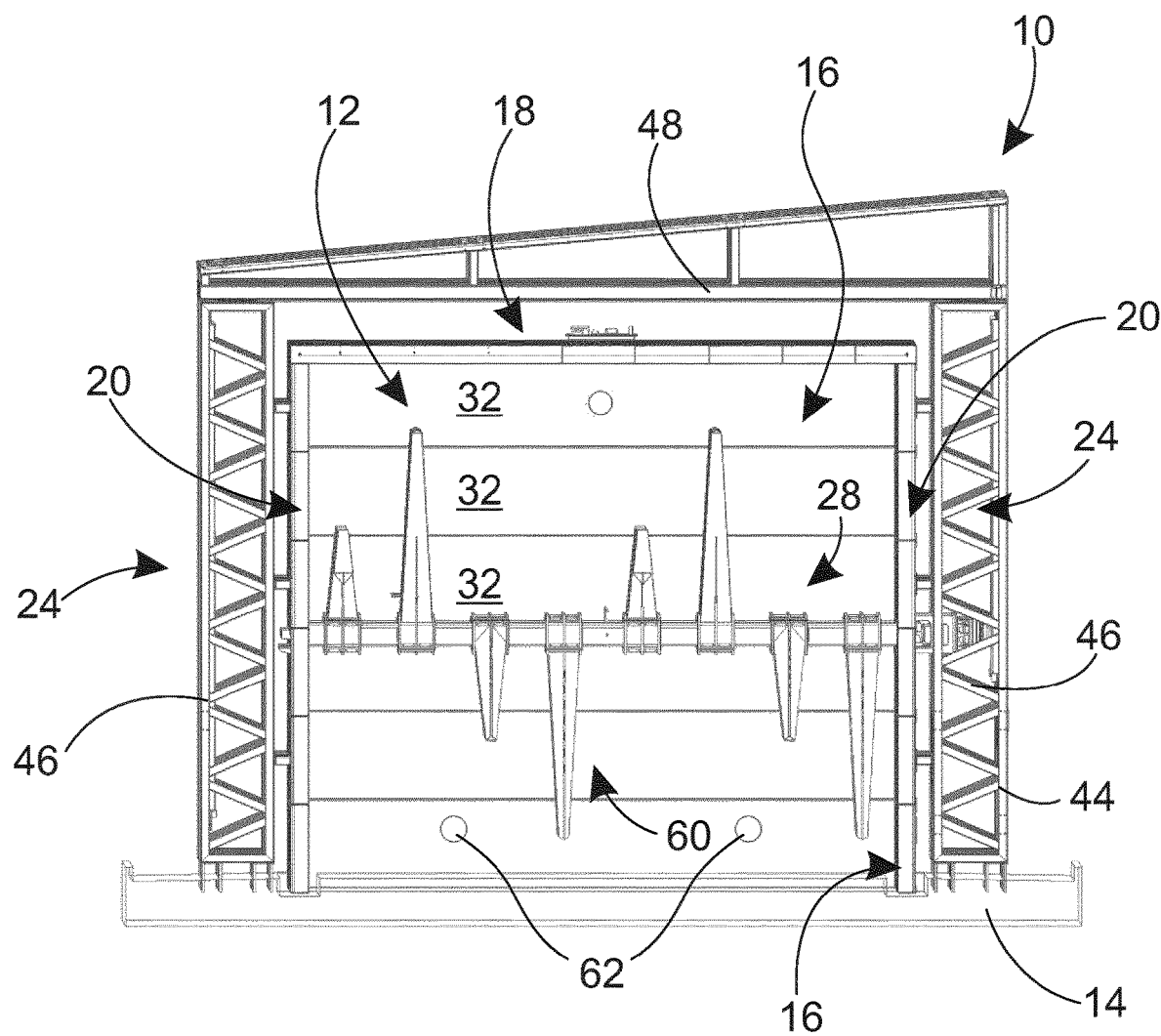
Figure 8:
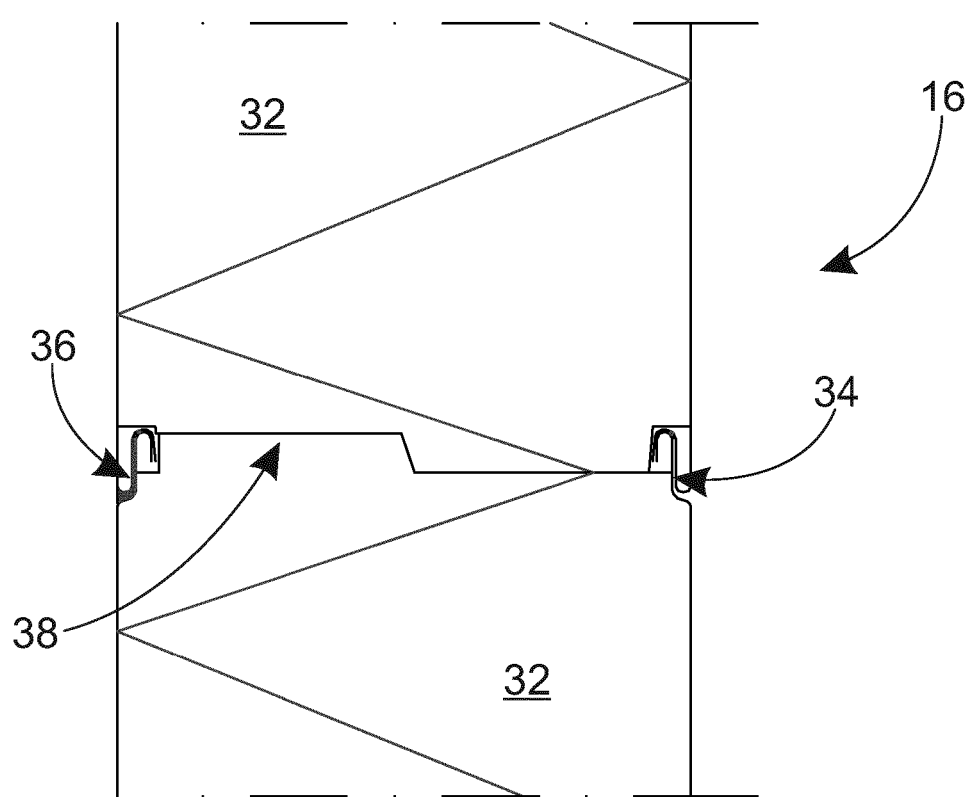
Figure 9A:
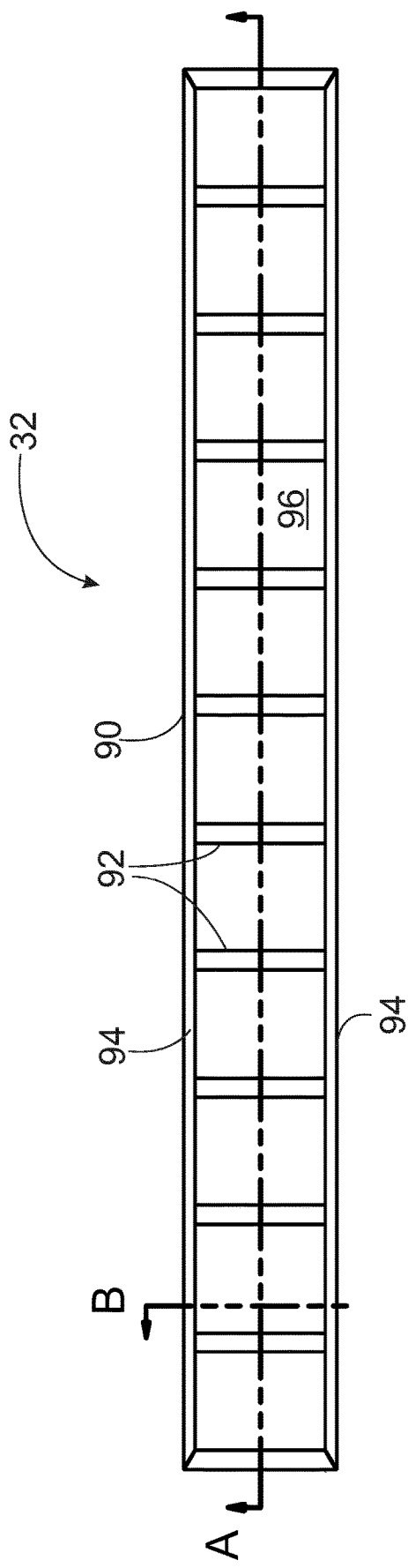
Figure 9B:
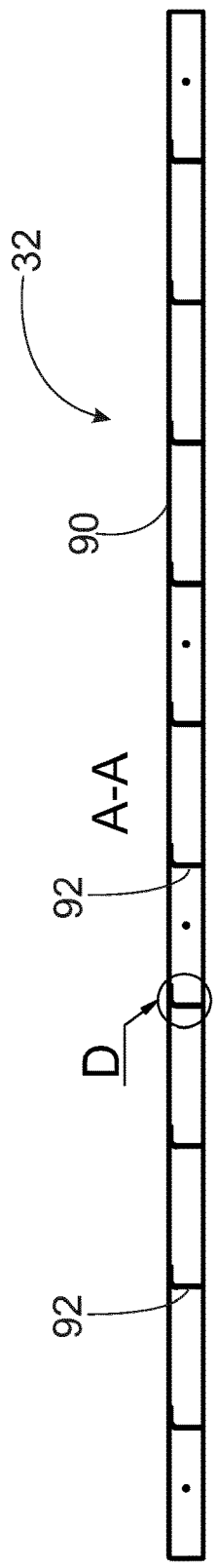
Figure 9C:
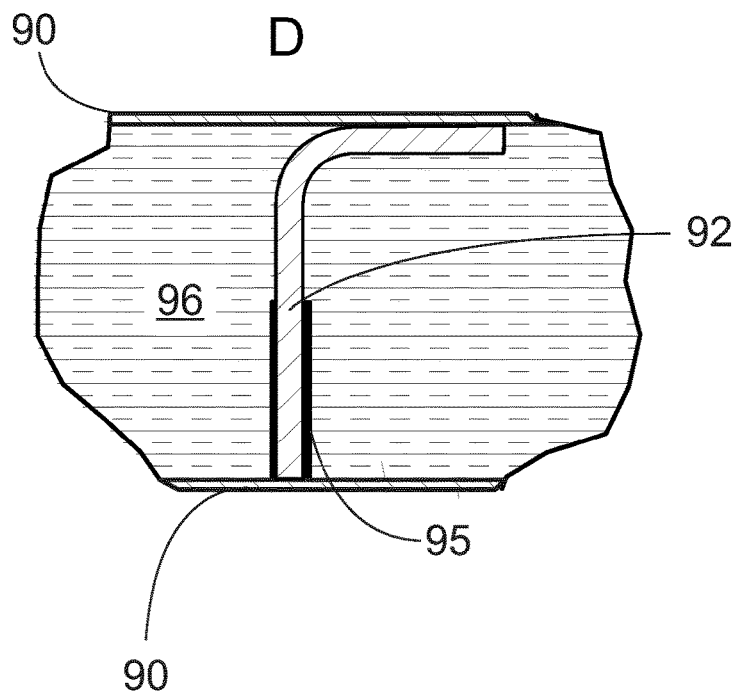
Figure 9D:
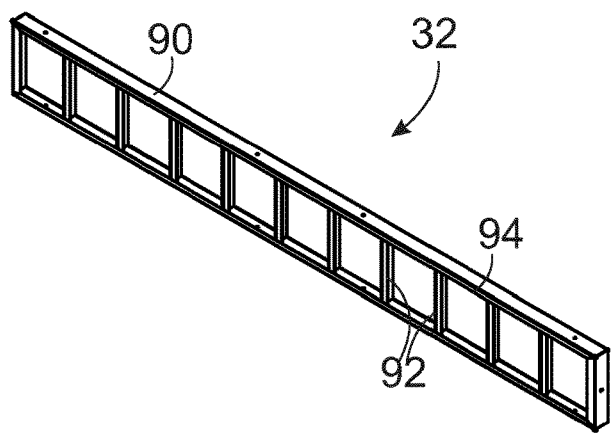
Figure 9E:
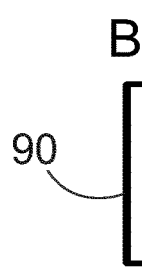
Figure 10:
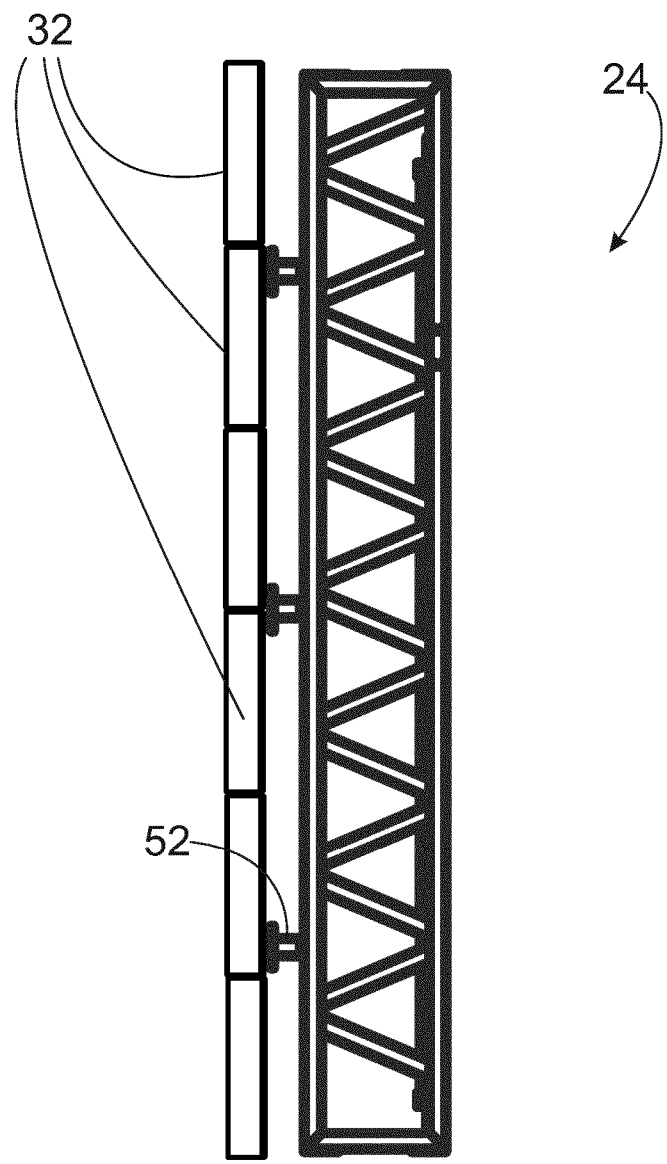
Figures 12A, 12B:
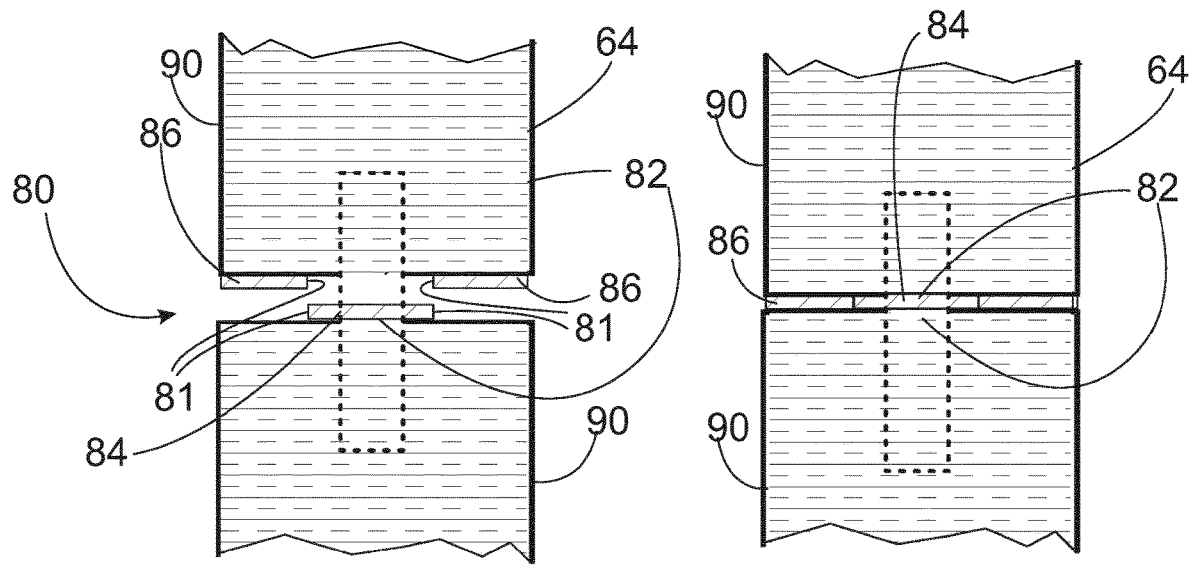
Figure 13:
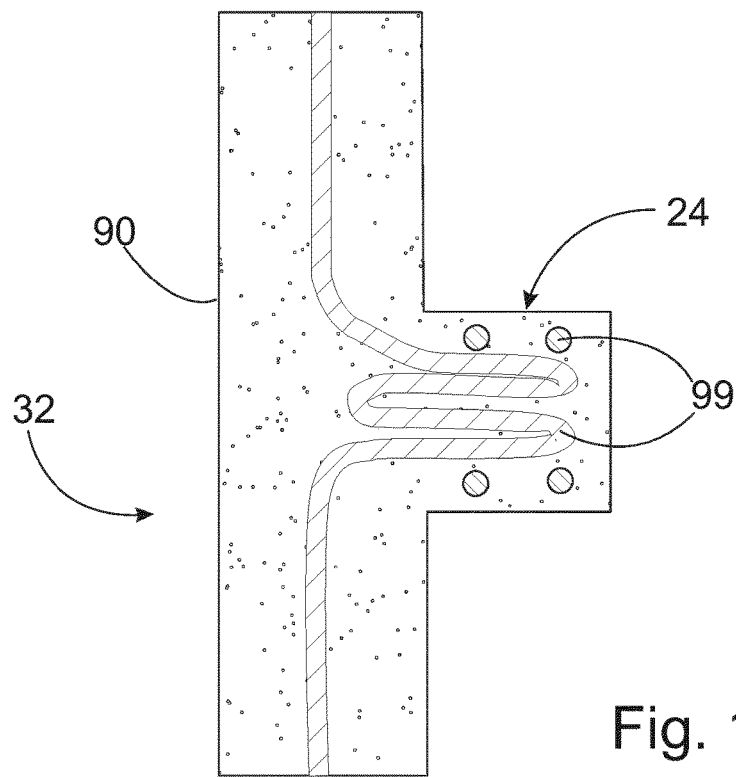

FIG. 3a is a side view of the reaction chamber assembled from elements of a reactor according to the invention, shown separated, FIG. 3b is an axonometric view of the reaction chamber assembled from elements of a reactor according to the invention, shown separated, FIG. 4a is an axonometric view of the external support frame structure of a reactor according to the invention, shown separated, FIG. 4b is an end view of the external support frame structure of a reactor according to the invention, shown separated, FIG. 4c is a side view of the external support frame structure of a reactor according to the invention, shown separated, FIG. 5 is an enlargement of FIG. 1, FIG. 6 is a top view of a reactor according to the invention, cut horizontally in the lengthwise direction relative to the frame, FIG. 7 is an end view of a reactor according to the invention, cut vertically in the transverse direction relative to the frame, FIG. 8 is a cross-sectional view of the joining of superimposed elements of the reaction chamber of a reactor according to the invention, FIG. 9a is a partially opened side view of an element of a reactor according to the invention, FIG. 9b is a cutaway top view of the cross-section A-A, i.e., of the element of FIG. 9a, FIG. 9c is the enlargement D of FIG. 9b, FIG. 9d is a partial cutaway axonometric view of an element, FIG. 9e is a longitudinal view of the element according to the cross-section B-B of FIG. 9a, FIG. 10 depicts the wall assembled from elements according to FIGS. 9a-9e of the reaction chamber of a reactor according to the invention, FIG. 11a depicts the support of the external support frame structure of the reactor according to the invention in another embodiment shown in lengthwise direction of the reactor chamber, FIG. 11b depicts the support of the external support frame structure of the reactor according to the invention in another embodiment shown in transverse direction of the reactor chamber, FIGS. 12a and 12b are superimposed cutaway views of the stages of the element locking shown in the direction of the elements, FIG. 13 is a cross-sectional view in the lengthwise direction relative to the element of a third embodiment of a reactor according to the invention, wherein the external support frame structure is integrated into the element.

A reactor 10 according to the invention comprises in all of its embodiments a tubular reaction chamber 12 with a substantially rectangular cross-section, an external support frame structure 24 and agitation and transfer equipment 28, illustrated in FIG. 1. The reaction chamber 12 is composed of a bottom 14, walls 16 connected thereto and a ceiling 18 connected to the walls 16. The reaction chamber naturally also includes inlet and outlet openings 62, via which raw material is supplied to the reaction chamber 12 advantageously with feed equipment included in the reactor. The external support frame structure 24 is arranged on the outer surface 22 included in the reaction chamber 12 for stiffening the reaction chamber 12. In FIGS. 1, 2, 4a-5, 7 and 10, the external support structure 24 is depicted as a lattice beam construction arranged at a distance from the reaction chamber 12. FIGS. 12a and 12b show another possible method for implementing the external support frame structure integrated into an element.

Advantageously, at least the walls 16 of the reaction chamber 12 are composed of modularly dimensioned elements 32, which are supported against horizontal forces acting within the reaction chamber using the external support frame structure 24. The locking of the elements 32 to the external support frame structure 24 can be implemented with edged reinforcements 23, which preferably circulate the elements 32 and between which it is possible to place plate stiffeners 20, from which the elements 32 are fastened to the external support frame structure 24 according to FIG. 2. Alternatively, the elements can be fastened to the external support frame structure with separate bondings on the surface of the elements, to which the external support frame structure is bolted.

Advantageously, the external support frame structure 24 includes plate stiffeners 20 arranged on the outer surface 22 of the reaction chamber 12 for stiffening the reaction chamber 12. The reaction chamber 12 with a substantially rectangular cross-section poorly resists, as a structure, loads generated by the internal pressure, which is why an external support frame structure 24 is necessary.

The reactor is meant for producing biogas via anaerobic digestion from organic raw material, such as household or agricultural waste. As a consequence of anaerobic digestion, the water content of raw material increases as digestion progresses and the water content of material in the reaction chamber is high, since the dry content of the material in the reaction chamber can preferably range between 10% and 35% by weight of dry matter. This high water content and the high filling rate of the reaction chamber lead to that the material generates hydrostatic pressure that acts on the walls of the reaction chamber and tends to push the walls of the reaction chamber outwards. The filling rate of the reaction chamber is preferably such that the liquid level extends to a distance of 0.1 m-0.5 m from the ceiling of the reaction chamber.

FIGS. 1-11b illustrate a first embodiment of a reactor according to the invention, wherein the reaction chamber 12 is formed by using modular elements 32. Modular elements are preferably 15 cm thick, 240 cm high and up to 1300 cm long components, which are connected to each other for forming at least the walls and preferably also the ceiling of the reaction chamber. In this context, when referring to walls, both the side walls and the end walls are meant. The elements can be so-called sandwich elements, which have, for example, steel casings and insulation between the casings. Insulation can be, for example, mineral wool or similar. The elements can be fastened to the wall element (shell) of the reactor with self-drilling screws.

FIGS. 9a-9e illustrate the structure of sandwich elements in more detail. The steel casing 90 of the element is advantageously bent from a steel sheet thus avoiding welding. Insulation 96 is preferably provided inside the casing 90. According to FIG. 9a, transverse steel profiles 92, which can be welded to the edge 94 of the casing 90, are arranged inside the casing 90. Advantageously, the steel profiles 92 are notched at the edges 94. Steel profiles stiffen the element. For example, steel profiles can be placed at an interval of 10 cm with the element length of 1.2 m. According to FIG. 9b, the shape of the steel profile 92 can be similar to an L shape when seen from above. The steel profile 92 can be connected to the casing at its ends with a weld joint 95, as well as alternatingly over the entire length of the profile. FIGS. 9d, 9e and 10 depict the element 32 in its operating position, wherein the lengthwise direction of steel profiles is the vertical direction. In FIG. 9c, the thicknesses of the casing 90 and the steel profile 92 are not correctly proportioned. The thickness of the casing may be 6 mm in elements that are located above the midpoint on the reaction chamber wall and 8 mm in elements below the midpoint, on which a higher hydrostatic pressure is exerted. The plate thicknesses of the lower-most elements are generally in the range of 6 mm-10 mm, when the reactor height is 5 m-12 m. In turn, the thickness of the steel profile can be 15 mm.

As an alternative to the use of modular elements, a reactor according to the invention can also be implemented using a reactor chamber that is welded as a complete tubular construction. In this case, transportation of a complete reaction chamber causes more costs than transportation of a reaction chamber assembled from elements on site, and transportation of a large reactor is only possible to an application site located in a well accessible region. An advantage of a reactor according to the invention when using this type of reaction chamber is that remarkable material savings are achieved, when the walls and the ceiling of the reaction chamber can be manufactured thinner than in prior art solutions.

According to FIG. 1, the external support frame structure 24 can be assembled from tubular beams 44, which form different parts in the external support frame structure 24. The external support frame structure 24 advantageously includes vertical columns 46 placed at a distance from each other on both sides of the reaction chamber 12, transverse support structures 48 connecting the vertical columns 46 on both sides of the reaction chamber 12 and longitudinal support structures 50 connecting the vertical columns 46 in the lengthwise direction relative to the reaction chamber 12. For example, tubular beams can be made of steel and have a diameter of 50 mm-150 mm and wall thickness of 2 mm-8 mm. Tubes are advantageously connected to each other with bolted joints and nuts. Tubes can also be made of stainless steel or composite.

Advantageously, each vertical column 46 includes at least two vertical supports 70 and transverse supports 72 arranged between them. The transverse supports 72 are advantageously set alternately in different directions so that the transverse supports 72 periodically connect to the vertical supports alternately. Such a construction of vertical columns 46 makes individual vertical columns independently rigid constructions in the lateral direction, which is particularly important when using a large reaction chamber. Thus, the distance from the vertical column 46 and the torque support of the base to the connection point between the vertical column 46 and the transverse support structure 48 located on top of the reaction chamber 12 becomes long; therefore, no external torque support exists in the central part of the vertical column against the transverse force generated by the pressure acting within the reaction chamber.

Figure 2:
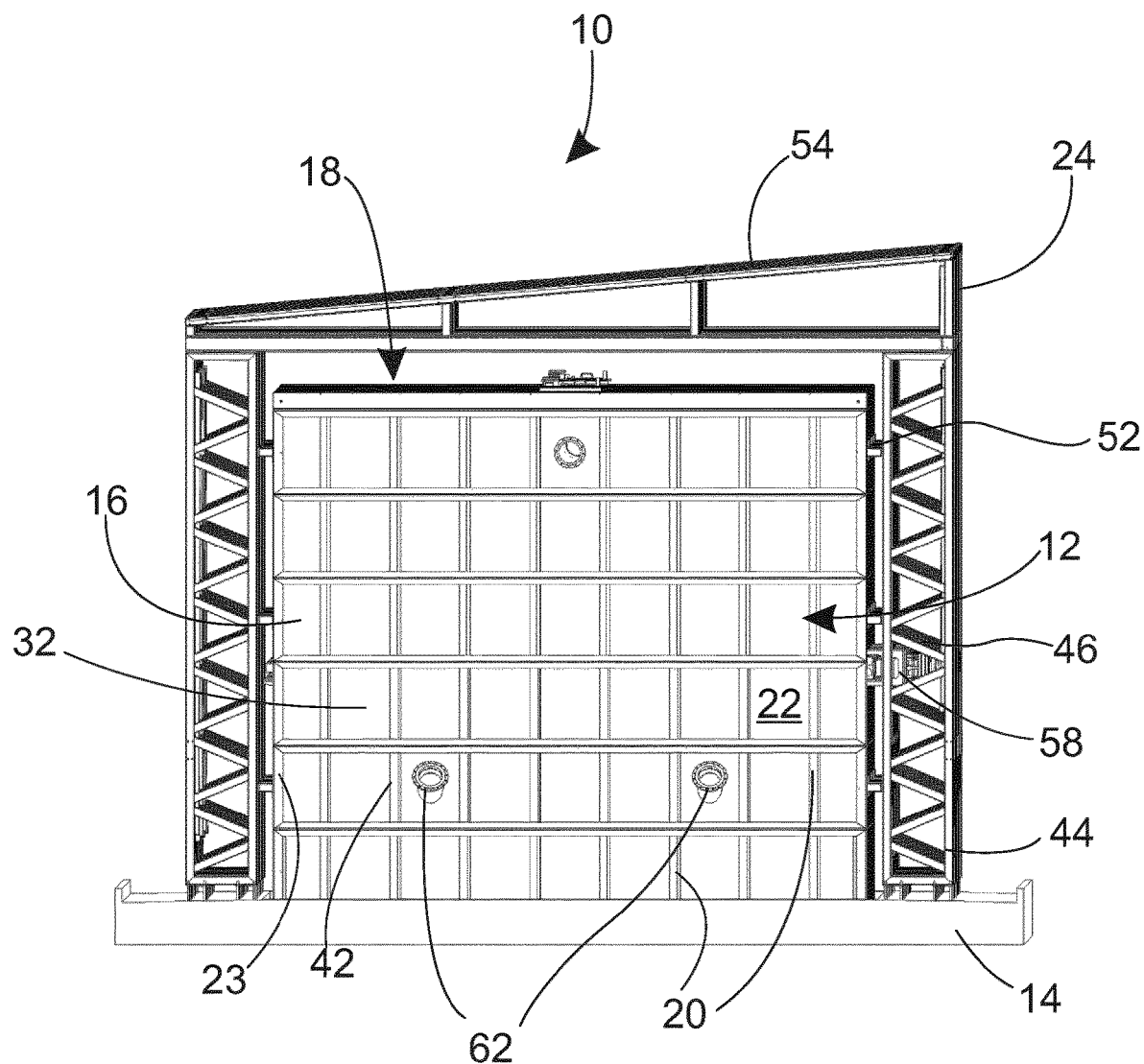
FIG. 2 is an end view of a reactor according to the invention.

FIG. 2 is an end view of a reactor 10 according to the invention. FIG. 2 shows how part of the external support frame structure 24 can be composed of vertical and transverse plate stiffeners 20, which are connected to each other and to the walls 16 of the reaction chamber 12. Advantageously, the plate stiffeners are sheet structures or angle irons 42, which are made of 6 mm-15 mm thick steel or stainless steel. The external support frame structure 24 is advantageously supported by its vertical columns 46 to the plate stiffeners 20 on the outer surface of the elements 32 via spacers 52. According to FIG. 2, the external support frame structure 24 advantageously also includes a ceiling structure 54 forming a pent roof, which can be covered with sheet metal, for example. The external support frame structure 24 is advantageously fixedly fastened to the bottom 14 of the reaction chamber 12, which can be, for example, a concrete slab cast on site. The fastening can be made, for example, using bondings made on the bottom or by bolting the external support frame structure to the bottom.

FIGS. 11a and 11b depict a particularly advantageous method for fastening the external support frame structure 24 to the slab functioning as the bottom 14 of the reaction chamber. The walls 16 of the reaction chamber 12 extend to the top surface level of the bottom 14; however, notches have been made on the slab for the external support frame structure 24 so that the external support frame structure 24 extends to a level 10 cm-40 cm lower than the bottom 14 of the reaction chamber 12. In addition, a cable 98 has been led through the bottom 14 in the transverse direction relative to it and connected between the vertical columns 46 of the support frame structure 24. The purpose of the cable 98 is to receive forces exerted on the external support frame structure 24 and in this way prevent the bottom end of the external support frame structure 24 from moving in the lateral direction due to the forces acting within the reaction chamber 12. Furthermore, the cable 98 can also be used at the top end of the vertical columns 46 of the external support frame structure 24 with the cable 98 passing by the reaction chamber 12. Thus, the cable 98 running above the reaction chamber 12 can replace the transverse support structure 48, shown in FIG. 4a, of the external support frame structure 24.

FIGS. 3a and 3b depict the reaction chamber 12 assembled of elements 32 of a reactor according to the invention, shown separated. In this embodiment, six elements are stacked on top of each other on the wall 16 of the reaction chamber 12. When the height of a single element is 120 cm, the height of the reaction chamber 12 will be 720 cm. Correspondingly, there are three elements 32 placed successively on the wall 16 of the reaction chamber 12, in which case, with a length of 11 mm for a single element, the length of the whole reaction chamber will be 33 m. Corresponding elements 32 can also be used placing them transversely on the ceiling 18 of the reaction chamber 12, in which case the width of the reaction chamber is 11 m. FIG. 3a depicts, shown with reference number 40, the lead-throughs of the agitation and transfer equipment preferably included in the reactor, through which the rotation axis 30 of the agitation and transfer equipment 28 is led, according to FIGS. 6 and 7. The ceiling 18 of the reaction chamber 12 may include transparent inspection doors 56, via which it is possible to monitor the filling rate and operation of the agitation and transfer equipment.

FIGS. 4a-4c depict the external support frame structure 24, shown separated. The external support frame structure 24 does not cover the entire surface area of the reaction chamber walls, but supports the reaction chamber walls via the plate stiffeners and edged reinforcements on the outer surface of the walls only at selected points. The vertical columns 46 in the external support frame structure 24 are evenly distributed at a distance from each other over the length of the reaction chamber; however, additional vertical columns 46 and transverse support structures 48 may also be included at both ends for extending the ceiling constructions slightly over the reaction chamber. Advantageously, at least one side of the external support frame structure 24 includes support irons 51 for a maintenance level, on which the maintenance level is formed. In the embodiment of FIGS. 1-8b, the vertical columns 46 are advantageously placed at an interval of 5 metres. The external support frame structure of the reactor according to the invention can be partly assembled already at the manufacturing site regarding, for example, vertical columns and transverse support structures, or alternatively, it is also easy to assemble the structures at the assembly site, since, due to bolted joints, erection of the external support frame structure does not require welding. Edged reinforcements and plate stiffeners are advantageously welded to the elements already during the manufacture of the elements in the factory.

FIG. 5 shows an enlargement of the reactor of FIG. 1. According to FIG. 5, the drive motors 58 and bearing assemblies 74 of the agitation and transfer equipment 28 can be supported to the elements 32 and their plate stiffeners 20 to allow easy maintenance of the drive motors 58 outside the reaction chamber 12. The number of agitation and transfer devices is the same as that of the agitation zones, since the material in the reaction chamber is agitated preferably as needed in each agitation zone.

FIG. 6 is a horizontal cross-sectional view showing how the rotation axis 30 of the agitation and transfer equipment 28 is supported with bearings 74 to the plate stiffeners 20 of the external support frame structure 24. FIG. 6 also shows the blade agitators 60 included in the agitation and transfer equipment 28. According to FIG. 6, the elements 32 forming the walls 16 of the reaction chamber 12 can be quite thin when there are, leaning immediately against these, plate stiffeners 20, which in turn lean against the vertical columns 46 of the external support frame structure 24.

FIG. 7 clearly illustrates how the vertical columns 46 of the external support frame structure support the plate stiffeners 20 on the outer surface 22 of the reaction chamber 12 via a spacer 52. In turn, the external support frame structure 24 can be fastened to bondings cast on the bottom 14.

FIG. 8 shows the seals 34 and 36 between the elements 32, stacked on top of each other preventing the material in the reaction chamber from exiting from the seam 38 between the elements 32 and, on the other hand, access of external moisture into insulation in the elements 34. On the inside, the seams can also be sealed with adhesive paste, for example, or by welding.

FIGS. 12a and 12b illustrate one advantageous method of implementing the joining of the elements 32 using bolted joints. The elements 32 include bolt holes 82, through which the bolts 64 are fitted. However, bolt holes 82 are the weakest point in the casing 90 of the element, and the casing 90 is easily damaged at the bolt holes 82 due to the effect of internal forces in the reaction chamber. This problem can be solved by welding reinforcement plates 84 and 86 to the bottom and surface of the element 32. Reinforcement plates are advantageously flat irons. At the bolt holes 82, a first reinforcement plate 86 is welded to one element in each joint and correspondingly, second reinforcement plates 84 circulating the first one are welded to the second element 32 of the joint. When placing the elements 32 on top of each other according to FIG. 11b, the reinforcement plates settle against each other for the part of the counter surfaces 81; therefore, lateral forces acting on the bolt holes 82 are received by the reinforcement plates. Thus, the material used for the casing of the elements 32 does not need to be so thick all over that it would resist stresses acting on the bolt holes.

FIG. 13 illustrates a second embodiment of a reactor according to the invention wherein the elements 32 forming the reaction chamber of the reactor are made of concrete by casting; that is, the elements can optionally be concrete casing elements. In this embodiment, the external support structure 24 is integrated into the element 32, on its outer edge, to support the concrete of the element. In this case, the external support structure 24 can be composed of longitudinal and vertical reinforcement irons 99. Thus, the reactor is not provided with an external support structure 24 arranged at a distance from the reaction chamber, similar to that shown in FIGS. 1-7, but this is replaced by an integrated external support structure outside the element 32.

A reactor design according to the invention implemented by using a thin reaction chamber and an external support frame structure can also be applied in other uses, wherein the reactor contains a large amount of material in a high water content, which generates a high hydrostatic pressure in a high reaction chamber.

While the present invention has been described in accordance with preferred compositions and embodiments, it is to be understood that certain substitutions and alterations may be made thereto without departing from the spirit and scope of the following claims.

We claim:

1. A reactor for manufacturing biogas from organic raw material using anaerobic digestion, comprising:
   the reactor having a tubular reaction chamber with a substantially rectangular cross-section composed of a bottom, walls and a ceiling for processing raw material into end products, and agitation and transfer equipment arranged in the reaction chamber, the reactor further having an external support frame structure arranged on the outer surface included in the reaction chamber for stiffening and supporting the reaction chamber externally against forces generated by raw material;
   the external support frame structure comprising
   vertical columns arranged at a distance from each other in the lengthwise direction relative to the reactor on both sides of the reactor,
   transverse support structures for connecting the vertical columns on each side of the reaction chamber in the transverse direction relative to the reactor, longitudinal support structures for connecting the vertical columns to each other in the lengthwise direction relative to the reactor on each side of the reactor, and each vertical column has two vertical supports at a distance from each other in the transverse direction relative to the reaction chamber and transverse supports arranged between the vertical supports.

2. A reactor according to claim 1, wherein the height of the reactor is 3 m-15 m.

3. A reactor according to claim 1 wherein the thickness of the walls of the reaction chamber is 100 mm-300 mm.

4. A reactor according to claim 1 wherein said reaction chamber has sealed lead throughs for the agitation and transfer equipment for keeping liquid raw material or end products in the reaction chamber.

5. A reactor according to claim 1 wherein said external support frame structure is composed of tubular beams connected to each other by welding.

6. A reactor according to claim 1 wherein said external support frame structure is composed of hollow tubes connected to each other.

7. A reactor according to claim 1, wherein the bottom of the reaction chamber includes footings for the vertical columns of the support frame structure.

8. A reactor according to claim 1, wherein the external support frame structure has spacers for supporting the vertical columns to plate stiffeners.

9. A reactor according to claim 1 wherein the bottom of the reaction chamber is made of concrete and the walls and the ceiling are steel structures.

10. A reactor according to claim 1 wherein the support frame structure is arranged to form the only horizontal support for the walls of said reaction chamber.

11. A reactor according to claim 1 wherein at least the walls of said reaction chamber are composed of modularly dimensioned elements.

12. A reactor according to claim 11, wherein the height of the modularly dimensioned elements on the wall of the reaction chamber is 1.0 m-3.6 m.

13. A reactor according to claim 11 wherein the length of the modularly dimensioned elements on the walls of the reaction chamber is 6 m-13 m.

14. A reactor according to claim 11 wherein the thicknesses of a steel casings of a lower-most elements of the reaction chamber are 2 mm-10 mm, when the height of the reactor is 5 m-12 m.

15. A reactor according to claim 11 wherein each element has an edged reinforcement arranged to circulate the element for reinforcing the element.

16. A reactor according to claim 11 wherein said elements are planar components.

* * * * *